(12) United States Patent
Biesmans et al.

(10) Patent No.: US 7,705,000 B2
(45) Date of Patent: Apr. 27, 2010

(54) ORAL SUSPENSION COMPRISING MELOXICAM

(75) Inventors: Caspar Peter Elisabeth Biesmans, Gooreind-Wuustwezel (BE); Bart De Spiegeleer, Gent (BE)

(73) Assignee: Janssen Pharmaceutica N.V., Beerse (BE)

( * ) Notice: Subject to any disclaimer, the term of this patent is extended or adjusted under 35 U.S.C. 154(b) by 288 days.

(21) Appl. No.: 11/720,869

(22) PCT Filed: Dec. 2, 2005

(86) PCT No.: PCT/EP2005/056419

§ 371 (c)(1),
(2), (4) Date: Jun. 5, 2007

(87) PCT Pub. No.: WO2006/061351

PCT Pub. Date: Jun. 15, 2006

(65) Prior Publication Data

US 2009/0221563 A1    Sep. 3, 2009

(30) Foreign Application Priority Data

Dec. 6, 2004    (EP) .................................. 04106318

(51) Int. Cl.
*A61K 31/535* (2006.01)
(52) U.S. Cl. ................................... 514/222.8
(58) Field of Classification Search ............... 514/222.8
See application file for complete search history.

(56) References Cited

U.S. PATENT DOCUMENTS

| 5,272,137 A | 12/1993 | Blase et al. |
| 5,409,907 A | 4/1995 | Blase et al. |

FOREIGN PATENT DOCUMENTS

| EP | 0405930 A | 8/1994 |
| EP | 0945134 A1 | 9/1999 |
| EP | 1 082 966 A | 3/2001 |
| EP | 0843998 A | 2/2002 |
| WO | WO 99/09988 A | 3/1999 |
| WO | WO 99/49845 A | 10/1999 |
| WO | WO 99/49867 A1 | 10/1999 |
| WO | WO 01/97813 A | 12/2001 |

OTHER PUBLICATIONS

Niazi, S. , *Handbook of Pharmaceutical Manufacturing*—liquid products, vol. 3 (2004).

*Primary Examiner*—Raymond J Henley, III
(74) *Attorney, Agent, or Firm*—Jeremy K McKown

(57) ABSTRACT

The present invention relates to an oral suspension comprising meloxicam, its preparation and its use in alleviating inflammation and pain in both acute and chronic musculo-skeletal disorders.

14 Claims, No Drawings

ORAL SUSPENSION COMPRISING MELOXICAM

CROSS REFERENCE TO RELATED APPLICATIONS

This application is the national stage of Application No. PCT/EP2005/056419, filed Dec. 2, 2005, which application claims priority from European Patent Appl. No. 04106318.1, filed Dec. 6, 2004.

The present invention relates to an oral suspension comprising meloxicam, its preparation and its use in alleviating inflammation and pain in both acute and chronic musculoskeletal disorders.

Meloxicam, 4-hydroxy-2-methyl-N-(5-methyl-2-thiazolyl)-2H-1,2-benzo-thiazine-3-carboxamide-1,1-dioxide, is a non-steroidal anti-inflammatory drug (NSAID) having selective cyclooxygenase-2 (COX-2) inhibitory properties. Due to its anti-inflammatory and analgesic properties, meloxicam is used to relieve the pain, tenderness, inflammation (swelling), and stiffness caused by arthritis and rheumatoid arthritis. For veterinary purposes meloxicam is used to control pain and inflammation (soreness) due to osteoarthritis in dogs. Osteoarthritis (OA) is a painful condition caused by "wear and tear" of cartilage and other parts of the joints that may result in the following changes or signs in dogs: limping or lameness, decreased activity or exercise (reluctance to stand, climb stairs, jump or run) stiffness or decreased movement of joints.

The use of a suspension for oral administration to animals is preferred as it is convenient and the dosage can be accurately controlled. In combination with an appropriate metering system, e.g. calibrated syringes or pipettes, an oral suspension provides high flexibility in controlling the dosage. This facilitates administration to animal species of different sizes or to different animal species or breeds, with varying dosage requirements. Additionally, an oral suspension allows the use of flavouring and/or palatability agents that can promote animal acceptance and compliance, which can be particularly advantageous when dosing chronically to animals.

Oral formulations comprising meloxicam have been described for instance in EP-1,066,029 as a suspension comprising meloxicam stabilized by the addition of highly dispersed silicon dioxide and small amounts of hydrophilic polymers to form a three-dimensional siloid structure. EP-1,299,107 discloses aqueous cyclodextrin-free solutions comprising meloxicam salts of an organic or inorganic base having a pH between 8.0 and 10.

Metacam® Oral Suspension is a commercial oral suspension comprising meloxicam available from Boehringer Ingelheim Vetmedica GmbH for reducing pain and inflammation in dogs suffering from osteoarthritis.

A particular aspect of liquid formulations for oral administration are the organoleptic properties of said oral formulations ensuring good palatability. At concentrations of over 0.5 mg/ml of meloxicam dissolved in solution, meloxicam has a noticeable unpleasant taste which cannot be adequately masked by the addition of bulk sweeteners or flavour correcting agents such as intense sweeteners, flavouring agents or taste masking agents. The solubility of meloxicam is pH-dependent and increases with increasing pH. At a pH of 4 the solubility of meloxicam is 0.5 µg/ml (see EP-0,945,134-A1 in Table 1 on page 3). Said solubility at a pH of 4 is well below the concentration level above which meloxicam gives a noticeable unpleasant taste. Hence the problem of meloxicam liquid formulations having an unpleasant bad taste can be solved by maintaining the pH of such liquid formulations in the range from 2 to 4. Since the solubility of meloxicam is very low in such liquid formulations with a pH value ranging from 2 to 4, meloxicam has to be formulated as a suspension. Since suspensions are formulations in which the active ingredient is in the form of a stable dispersion of fine particles in water or organic liquid, suspensions inherently suffer from the problem of caking of the individual particles leading to sedimentation or precipitation of the suspended active ingredients.

It has now been found that when meloxicam is suspended in an aqueous glycerol mixture which further comprises a thickening agent, one or more taste modifying agents and a buffer system for maintaining the pH in a range from 2 to 4, the resulting suspensions do not have the unpleasant taste problem and have been demonstrated to be free of caking or irreversible sedimentation of meloxicam in storage stability tests. The meloxicam suspensions of the present invention are free or essentially free of silicon dioxide. In the context of the invention, the phrase "free or essentially free of silicon dioxide" means that no silicon dioxide is deliberately added to the instant suspension in order to achieve the stabilisation.

The oral suspensions of the present invention comprise meloxicam suspended in an aqueous glycerol mixture wherein the amount of glycerol ranges from 5% v/v to 30% v/v, preferably from 10% v/v to 20% v/v based on the total volume of the suspension.

The thickening agent is used to increase the viscosity of the oral suspension. Essentially any suitable thickening agent can be used. In practice the thickening agent is selected from the group consisting of methylcellulose, hydroxyethylcellulose, hydroxypropylcellulose, hydroxypropylmethylcellulose, hydroxy ethyl propyl cellulose, starches (such as maize or corn starch, potato starch, rice starch, tapioca starch, and wheat starch), carboxyvinyl polymers (carbomers such as Carbopol®), carboxymethyl cellulose and salts thereof, microcrystalline cellulose and arabic gum, guar gum, and xanthan gum, and mixtures thereof. A preferred thickening agent is microcrystalline cellulose which is commercially available as Avicel®. Some forms of Avicel® such as Avicel® RC591 are mixtures of microcrystalline cellulose with carboxymethyl cellulose (which typically contains 87-91% microcrystalline cellulose and 9-13% carboxy methylcellulose sodium). Another preferred thickening agent is xanthan gum. More preferred are mixtures of microcrystalline cellulose and xanthan gum.

The thickening agent may also contribute to the adhesive properties of the suspension, making it stick to feed and/or oral mucosa.

The thickening agent can be used in a concentration effective to increase the viscosity of the oral suspension to the desired extent, for example, about 2 mg/ml to about 20 mg/ml, preferably about 5 mg/ml to about 15 mg/ml.

Another art known agent for increasing the viscosity of a suspension or dispersion is silicon dioxide, see e.g. EP-1,066,029. The oral suspensions of the present invention however are free or essentially free of silicon dioxide.

Taste modifying agents suitable for use in the oral solutions of the present invention include: bulk sweeteners, intense sweeteners, and flavouring agents. Examples of bulk sweeteners are sorbitol, mannitol, fructose, sucrose, maltose, isomalt, glucose, hydrogenated glucose syrup, and xylitol, and mixtures thereof. Examples of intense sweeteners are saccharin, aspartame, acesulfame, cyclamate, alitame, a dihydrochalcone sweetener, monellin, neohesperidin, neotame, stevioside and sucralose, the pharmaceutically acceptable salts thereof such as sodium or calcium saccharin, acesulfame potassium or sodium cyclamate, and mixtures thereof.

Examples of flavouring agents are cherry, raspberry, black currant, strawberry flavour, caramel chocolate flavour, mint cool flavour, fantasy flavour, meat flavours and the like.

In an embodiment of the present invention the one or more taste modifying agents are a combination of a bulk sweetener and an intense sweetener. A preferred bulk sweetener is sorbitol. A preferred intense sweetener is sodium saccharin. The bulk sweetener is present in an amount ranging from 50 mg/ml to 500 mg/ml, preferably from 100 mg/ml to 250 mg/ml. The intense sweetener is present in an amount ranging from 1 mg/ml to 50 mg/ml, preferably from 2.5 mg/ml to 10 mg/ml.

The buffer system for maintaining the pH of the meloxicam suspensions in the range from 2 to 4 comprises an aqueous mixture of an appropriate amount of an acid such as phosphoric, succinic, tartaric, lactic, or citric acid, and a base, in particular sodium hydroxide, disodium hydrogen phosphate or sodium hydrogen carbonate.

In an embodiment of the present invention meloxicam is used in a micronised form wherein the $dl_{50}$ of the micronised meloxicam particles ranges from 1 to 20 μm. The $dl_{50}$ refers to the diameter below which 50% of the volume distribution occurs.

The amount of meloxicam in the oral suspensions of the present invention ranges from 0.5 mg/ml to 5.0 mg/ml, preferably from 1.0 mg/ml to 2.0 mg/ml, more preferably about 1.5 mg/ml.

In order to protect the oral suspensions of the present invention from microbial contamination during use, a preservative can be added. This preservative is preferably selected from the group consisting of benzoic acid and the sodium or potassium salts thereof, sorbic acid and the sodium or potassium salts thereof, benzyl alcohol, methyl parahydroxybenzoate, ethyl para-hydroxybenzoate, propyl parahydroxybenzoate, butyl parahydroxybenzoate and mixtures thereof. A preferred preservative is sodium benzoate. The preservative is present in an amount ranging from 0.2 mg/ml to 5.0 mg/ml, preferably from 0.5 mg/ml to 2.0 mg/ml, more preferably about 1.0 mg/ml.

In view of the selective cydooxygenase-2 (COX-2) inhibitory properties of meloxicam and its concomitant anti-inflammatory and analgesic properties, the oral suspensions of the present invention are suitable to alleviate the pain, tenderness, inflammation (swelling), in both acute and chronic musculo-skeletal disorders in warm-blooded animals, in particular companion animals, especially dogs and cats. Said acute and chronic musculo-skeletal disorders are for instance arthritis, rheumatoid arthritis or osteoarthritis.

Accordingly the present invention also provides oral suspensions comprising meloxicam for the manufacture of a medicament for alleviating pain, tenderness, inflammation (swelling), in both acute and chronic musculo-skeletal disorders in warm-blooded animals, in particular companion animals, especially dogs and cats.

The present invention further provides a method of alleviating pain, tenderness, inflammation (swelling), in both acute and chronic musculo-skeletal disorders in warm-blooded animals which comprises administering to an animal in need of such treatment an oral suspension of the present invention comprising a therapeutically effective amount of meloxicam.

The oral suspensions of the present invention may also be used for the reduction of post-operative pain and inflammation following orthopaedic and soft tissue surgery. Accordingly an oral suspension comprising meloxicam for the manufacture of a medicament for the reduction of post-operative pain and inflammation following orthopaedic and soft tissue surgery is provided.

The term "therapeutically effective amount of meloxicam" as used herein, means that amount of meloxicam that elicits the biological or medicinal response in the animal that is being sought by the veterinarian, which includes alleviation of the symptoms of the condition being treated. The therapeutically effective amount can be determined using routine optimization techniques and is dependent upon the particular condition to be treated, the condition of the animal, the route of administration, the formulation, and the judgment of the practitioner and other factors evident to those skilled in the art. An effective amount may be achieved by multiple dosing.

The oral suspensions of the present invention are administered in such an amount that a single daily dosage comprises from 0.05 mg to 1.0 mg of meloxicam per kilogram bodyweight. In practice a typical once daily dosage ranges from 0.1 to 0.2 milligram of meloxicam per kilogram bodyweight.

The oral suspensions of the present invention can be administered directly in the oral cavity or more preferably mixed with the food. Dosing of the oral suspensions can be done using an appropriate metering system such as e.g. a calibrated syringe, pipette, or a pre-filled dispenser that can deliver calibrated amounts of fluid.

FORMULATION EXAMPLES

| Formulation 1 | |
|---|---|
| Micronised meloxicam | 0.15% w/v |
| Glycerol | 12.50% v/v |
| Avicel RC591 | 1.00% w/v |
| Xanthan gum | 0.25% w/v |
| Sodium benzoate | 0.10% w/v |
| Sorbitol | 17.50% w/v |
| Sodium saccharin | 0.50% w/v |
| Citric acid | 1.92% w/v |
| Sodium hydroxide (10% solution) | pH adjustment to pH = 3.85 |
| Water | up to 100 ml |

Formulation 1 was prepared by dissolving citric acid (28.8 g), sodium benzoate (1.5 g), sodium saccharin (7.5 g), and sorbitol (262.5 g) in water (800 ml) while stirring to obtain a homogeneous mixture. Avicel RC591 (15 g) and xanthan gum (3.75 g) were added to the aqueous mixture while stirring. A 10% NaOH solution was added to adjust the pH to 3.85 and an additional 52.5 ml of water was added for final volumetric adjustment. Meloxicam (2.25 g) was dissolved in glycerol (237.0 g) while stirring to obtain a homogeneous mixture. The aqueous mixture was then slowly added to the glycerol mixture while stirring to obtain a homogenous suspension and water was added for final volumetric adjustment to a total volume of 1500 ml.

Other formulations prepared following the same procedure as Formulation example 1.

| Ingredient | Example 2 Amount | Example 3 Amount | Example 4 Amount | Example 5 Amount |
|---|---|---|---|---|
| meloxicam | 150 mg | 150 mg | 150 mg | 150 mg |
| glycerol | 12.5 ml | 12.5 ml | 12.5 ml | 12.5 ml |
| Avicel RC591 | — | 0.5 g | 0.5 g | — |
| xanthan gum | 0.25 g | 0.125 g | — | 0.125 g |
| C*Hiform 12742 | 1 g | — | 0.5 g | 0.5 g |
| sodium benzoate | 0.1 g | 0.1 g | 0.1 g | 0.1 g |
| sorbitol | 17.5 g | 17.5 g | 17.5 g | 17.5 g |
| sodium saccharin | 1 g | 1 g | 1 g | 1 g |

-continued

| Ingredient | Example 2 Amount | Example 3 Amount | Example 4 Amount | Example 5 Amount |
| --- | --- | --- | --- | --- |
| citrid acid | 1.92 g | 1.92 g | 1.92 g | 1.92 g |
| water | up to 100 ml | up to 100 ml | up to 100 ml | up to 100 ml |

All formulations were pH adjusted to a pH of 3.85 with a sodium hydroxide solution (10% w/v). C*Hiform 12742 is a commercially available cold water swelling waxy maize starch or tapioca starch from Cerestar.

The oral suspensions of the present invention can in general be prepared by
a) dissolving the appropriate amounts of thickening agent and the one or more taste modifying agents in water followed by the addition of the buffer system to adjust the pH in the range from 2 to 4;
b) dissolving the appropriate amount of meloxicam in glycerol; and
c) adding the aqueous mixture of step a) to the glycerol mixture of step b) while stirring to obtain a homogeneous suspension.

The plasma kinetics of the oral suspension as described in Formulation example 1 have been compared with those of the commercially available reference product Metacam® Oral Suspension in a comparative study. This GLP comparative study was carried out with 16 Beagle dogs following a parallel administration design with eight animals per treatment group. Both formulations were administered at the dose of 0.2 mg/kg body weight on the first day of treatment, followed by a maintenance dose of 0.1 mg/kg body weight for another four consecutive days. Meloxicam in plasma was quantified by using an analytical HPLC procedure validated according to the FDA Guidance Bioanalytical Method Validation. The pharmacokinetic profile of both formulations showed no significant differences which led to the conclusion the oral suspension of Formulation example 1 is bio-equivalent to the commercially available Metacam® Oral Suspension.

Storage Stability Test

The storage stability of the meloxicam suspension of Formulation example 1 has been tested over a 6 month storage period. Said meloxicam suspension was kept in a glass vial at a temperature of 40° C. and 75% relative humidity.

At the end of the 6 month storage period the composition of said suspension was analysed by HPLC chromatography and the amount of meloxicam and its known impurities as described in the Britisch Pharmacopoeia was determined. No increase in impurities was observed nor a decrease of meloxicam.

During the 6 month storage period, it was observed that meloxicam started to settle at the bottom of the vial. Inverting the vial a couple of times resuspended any settled meloxicam yielding a homogeneous suspension. No irreversible caking was observed. Furthermore microscopic pictures were taken and based upon qualitative visual comparison the number of particles observed, as well as the typical particle sizes, remained unchanged during the 6 month storage period.

The invention claimed is:

1. A suspension comprising meloxicam suspended in an aqueous glycerol mixture, a thickening agent, one or more taste modifying agents and a buffer system for maintaining the pH in a range from 2 to 4, wherein the suspension is free or essentially free of silicon dioxide.

2. A suspension as claimed in claim 1 comprising
a) meloxicam in an amount ranging from 0.5 mg/ml to 5.0 mg/ml;
b) a thickening agent selected from the group consisting of methylcellulose, hydroxyethylcellulose, hydroxypropylcellulose, hydroxypropylmethylcellulose, hydroxy ethyl propyl cellulose, starches, carboxyvinyl polymers, carboxymethyl cellulose and salts thereof, microcrystalline cellulose and arabic gum, guar gum, xanthan gum, and mixtures thereof;
c) one or more taste modifying agents selected from the group consisting of bulk sweeteners, intense sweeteners, flavouring agents, and mixtures thereof;
d) a buffer system comprising of an aqueous mixture of an acid wherein the acid is phosphoric, succinic, tartaric, lactic, or citric acid, and a base, wherein the base is sodium hydroxide, disodium hydrogen phosphate or sodium hydrogen carbonate, for maintaining the pH in the range from 2 to 4; and
e) water and glycerol wherein the amount of glycerol ranges from 5% v/v to 30% v/v based on the total volume of the suspension.

3. A suspension as claimed in claim 2 wherein meloxicam is present in micronised form wherein the $dl_{50}$ of the micronised meloxicam particles ranges from 1 to 20 μm.

4. A suspension as claimed in claim 3 wherein the thickening agent is present in an amount ranging from 2 mg/ml to 20 mg/ml.

5. A suspension as claimed in claim 4 wherein the thickening agent is xanthan gum, or microcrystalline cellulose, or a mixture thereof.

6. A suspension as claimed in claim 3 wherein the one or more taste modifying agents are a combination of a bulk sweetener present in an amount ranging from 50 mg/ml to 500 mg/ml and the intense sweetener is present in an amount ranging from 1 mg/ml to 50 mg/ml.

7. A suspension as claimed in claim 6 wherein the bulk sweetener is sorbitol and the intense sweetener is sodium saccharin.

8. A suspension as claimed in claim 3 wherein the buffer system is an aqueous mixture of citric acid and sodium hydroxide.

9. A suspension as claimed in claim 3 further comprising a preservative selected from the group consisting of benzoic acid and the sodium or potassium salts thereof, sorbic acid and the sodium or potassium salts thereof, benzyl alcohol, methyl parahydroxybenzoate, ethyl parahydroxybenzoate, propyl parahydroxybenzoate, butyl parahydroxybenzoate and mixtures thereof.

10. A suspension as claimed in claim 9 wherein the preservative is sodium benzoate present in an amount ranging from 0.2 mg/ml to 5.0 mg/ml.

11. A suspension as claimed in claim 3 comprising as thickening agent a mixture of microcrystalline cellulose and xanthan gum in an amount of 5 mg/ml to 15 mg/ml; as taste modifying agents a mixture or sorbitol in an amount of 100 mg/ml to 250 mg/ml and sodium saccharin in an amount of 2.5 mg/mi to 10 mg/ml; and an aqueous glycerol mixture wherein the amount of glycerol ranges from 10% v/v to 20% v/v based on the total volume of the suspension.

12. A suspension as claimed in claim 11 further comprising sodium benzoate as a preservative in an amount of 0.5 mg/ml to 2.0 mg/ml.

13. A process for preparing a suspension according to claim 1 comprising:
   dissolving the appropriate amounts of thickening agent and the one or more taste modifying agents in water followed by the addition of the buffer system to adjust the pH in the range from 2 to 4;
   b) dissolving the appropriate amount of meloxicam in glycerol; and
   c) adding the aqueous mixture of step a) to the glycerol mixture of step b) while stirring to obtain a homogeneous suspension.

14. A method for alleviating pain and inflammation in both acute and chronic musculo-skeletal disorders, comprising, administering a suspension according to claim 1.

* * * * *

UNITED STATES PATENT AND TRADEMARK OFFICE
CERTIFICATE OF CORRECTION

| | | |
|---|---|---|
| PATENT NO. | : 7,705,000 B2 | Page 1 of 1 |
| APPLICATION NO. | : 11/720869 | |
| DATED | : April 27, 2010 | |
| INVENTOR(S) | : Biesmans et al. | |

It is certified that error appears in the above-identified patent and that said Letters Patent is hereby corrected as shown below:

<u>Column 7</u>

Line 3, insert -- a) -- before "dissolving"

Signed and Sealed this

Twenty-first Day of December, 2010

David J. Kappos
*Director of the United States Patent and Trademark Office*